United States Patent [19]
Gertzman

[11] 3,991,754
[45] Nov. 16, 1976

[54] SURGICAL ADHESIVE TAPE

[75] Inventor: Arthur A. Gertzman, Bridgewater, N.J.

[73] Assignee: Ethicon, Inc., Somerville, N.J.

[22] Filed: Sept. 15, 1975

[21] Appl. No.: 613,157

[52] U.S. Cl. .............................................. 128/156
[51] Int. Cl.² ........................................ A61L 15/00
[58] Field of Search ........................... 128/155–157, 128/169–170; 428/265–269

[56] References Cited
UNITED STATES PATENTS

| | | | |
|---|---|---|---|
| 3,364,063 | 1/1968 | Satas | 128/156 X |
| 3,794,548 | 2/1974 | Wirth et al. | 428/267 |
| 3,814,101 | 6/1974 | Kozak | 128/156 X |
| 3,824,996 | 7/1974 | Carlisle | 128/156 |
| 3,870,041 | 3/1975 | Davies | 128/156 |

*Primary Examiner*—Lawrence W. Trapp
*Attorney, Agent, or Firm*—Wayne R. Eberhardt

[57] ABSTRACT

A breathable, moisture vapor permeable pressure sensitive adhesive tape comprising a patterned, fibrillated polymeric film having 10 to 70 percent open area, coated on one side with a non-irritating pressure sensitive surgical adhesive. The polymeric film is composed of a plurality of substantially parallel monofilament strands interconnected by a plurality of fibrils. The physical structure of the tape combines good straight tensile strength with ease of tearability in two directions. The tape is permeable to both air and water vapor, and is substantially unaffected by contact with liquid water or body fluids. The tape is particularly useful for wound closure in certain surgical procedures.

23 Claims, 7 Drawing Figures

U.S. Patent    Nov. 16, 1976    3,991,754
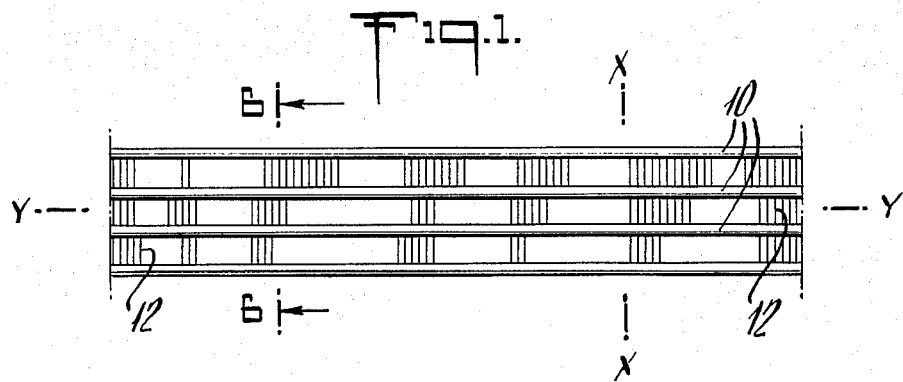
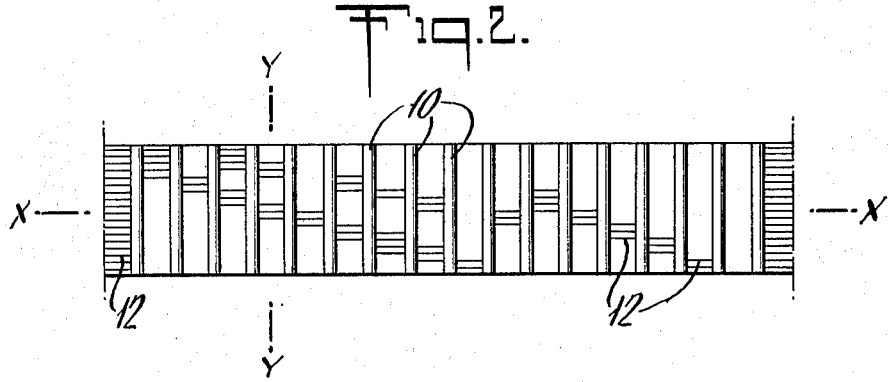
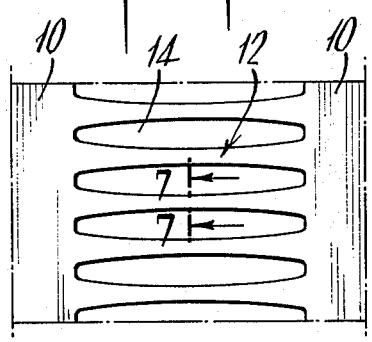 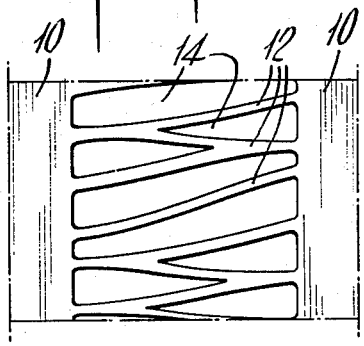 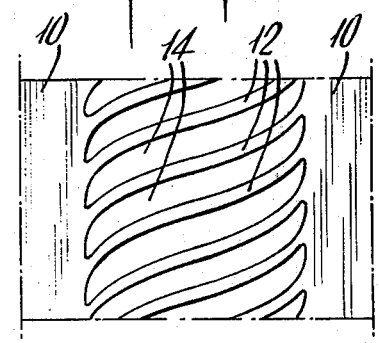
 

SURGICAL ADHESIVE TAPE

BACKGROUND OF THE INVENTION

1. Field of the Invention

This invention relates to a new and useful porous, pressure sensitive adhesive tape, and more particularly to a surgical tape comprising a highly porous plastic film backing material coated on one side with a pressure sensitive adhesive.

2. Description of Prior Art

It has long been known that surgical adhesive tape should be permeable to water vapor in order to prevent maceration of the wound site due to occlusion of water arising from transepidermal discharge of moisture from the body. A substantially non-porous tape which interferes with this essential body function may result in severe skin irritation.

In addition to being porous or breathable, surgical tapes are also desirably finger tearable so that strips of tape may be torn rather than cut to a size suitable for the particular wound. The tape must have sufficient tensile strength however, to restrain the wound in an immobile position for healing, and sufficiently flexible to conform to the surface of the skin and to move with movement of the skin.

Surgical tapes of the prior art have been constructed of a variety of backing materials and adhesives. Porous backing materials of woven or non-woven fabrics and perforated plastic films have been suggested in U.S. Pat. Nos. 3,039,893 and 3,523,846. Another porous backing formed of non-woven rayon textile fiber is described in U.S. Pat. No. 3,121,021. Microporous films of plasticized polyvinyl chloride and woven, non-woven, and knitted fabrics are described in U.S. Pat. No. 3,645,835.

Plastic films are desirable as backing materials because they are light, flexible, thin, transparent and easily cleanable. Except for certain limited microporous plastic compositions, porosity of plastic films has typically been obtained mechanically by punching holes in the film. Such perforated films of the prior art have generally lacked the combination of high porosity, dimensional stability, tensile strength, and tearability required of a surgical tape.

It is accordingly an object of the present invention to provide an improved surgical tape having a porous plastic backing material. It is a further object of this invention to provide a porous surgical tape which is substantially unaffected by moisture or body fluids and has good dimensional stability, flexibility, and tensile strength. It is also an object of this invention to provide a plastic surgical tape which is biaxially oriented and readily tearable in two directions. Yet other objects of this invention will be apparent from the ensuing description and claims.

SUMMARY

The surgical tape of the present invention utilizes a polymer film backing material consisting of a plurality of substantially parallel monofilaments with adjacent monofilaments connected by a plurality of fibrils. The backing material may be formed by embossing striations in the film in one axial direction, then subjecting the film to mechanical stress in a transverse direction in order to fibrillate the striated portions of the film and produce a multitude of fibrils extending between adjacent monofilaments.

The fibrillated film has an open area of 10 to 70 percent and is readily permeated by air and liquids. The film is bilaterally tearable in directions corresponding to the orientation of the monofilaments and the interconnecting fibrils. The film is dimensionally stable with good tensile strength and is unaffected by moisture or body fluids.

The fibrillated film is coated with a thin layer of any conventional non-toxic, pressure sensitive surgical adhesive to produce the final surgical tape.

DESCRIPTION OF DRAWINGS

FIG. 1 is a plan view of a plastic backing material with the monofilaments oriented parallel to the longitudinal axis of the surgical tape.

FIG. 2 is a plan view of a plastic backing material with the monofilaments oriented at right angles to the longitudinal axis of the surgical tape.

FIG. 3 is an enlarged plan view showing the detail of fibrils interconnecting two parallel monofilaments.

FIG. 4 is an enlarged plan view showing a network of fibrils connecting two parallel monofilaments.

FIG. 5 is an enlarged plan view showing fibrils connecting two parallel monofilaments.

FIG. 6 is an enlarged view in cross-section of a fibrillated plastic film having an adhesive coating thereon.

FIG. 7 is an enlarged view in cross-section of typical fibril structures.

DESCRIPTION OF PREFERRED EMBODIMENTS

Referring now to FIGS. 1 and 2, the monofilament strand 10 of the fibrillated film may run parallel to or transverse to the longitudinal axis of the surgical tape. Fibrils 12 interconnecting monofilament strand 10 are preferably at substantially right angles to the monofilaments as shown in FIG. 3. This structure of the film and orientation of the fibrils and monofilaments gives the film bilateral tearability with tear lines following either a single monofilament or a line of fibrils traversing several monofilaments. A given length of tape may accordingly be narrowed and/or shortened to accommodate a given application by tearing, for example along lines X—X or Y—Y of FIG. 1.

Monofilament strands 10 in the plastic film may have a thickness of from about 0.05 to 0.5 mm and preferably from about 0.1 to about 0.3 mm. Films within this range of thickness have a desirable combination of flexibility, tearability and tensile strength. These films also lend themselves to mechanical processing whereby the fibrils are developed.

Fibrillated films useful as backing materials in the present invention may be prepared by a method wherein a sheet of plastic is embossed with parallel lines, preferably following the longitudinal axis of the films, and the embossed film is then laterally expanded with mechanical working in order to stretch and fibrillate the area of the embossed lines and obtain a plurality of substantially parallel continuous monofilaments in a spaced apart side-by-side relationship with adjacent monofilaments being interconnected by a plurality of fibrils. A suitable method is described in detail in U.S. Pat. No. 3,705,070, incorporated herein by reference. Suitable films useful in the preparation of surgical tapes in accordance with the present invention are commercially available from Hercules, Inc. under the tradename "Delnet."

The structure of the fibrillated portion of the film may vary as to size, spacing, and configuration of the fibrils. In a preferred embodiment illustrated in FIG. 3, fibrils 12 are uniformly spaced parallel to each other and perpendicular to monofilaments 10. The fibrils may, however, assume other less regular configurations without significantly detracting from the performance or desirable features of the film. The fibrils may, for example, be somewhat interconnected and web-like as illustrated in FIG. 4. The fibrils may also be angular rather than perpendicular with respect to the monofilaments as illustrated in FIGS. 4 and 5 in which case the tape will characteristically tear on a bias across the monofilaments.

While the particular shape or configuration of the interconnecting fibrils is not critical to the present invention, it is desirable that the fibrils be spaced so that the average overall open area of the tape is from about 10 to 70 percent, and most preferably from 25 to 55 percent. At least about 10 percent open area is required in tapes of the present construction to permit liquid and vapor transfer adequate to prevent maceration of the underlying skin. At more than about 70 percent open area, the tape loses strength and dimensional stability and the solid area is insufficient for good adhesive coating. In the range of 25 to 55 percent open area, the tape is dimensionally stable, sufficiently porous for the transfer of gas and water vapor from the wound site, and has sufficient surface area density to provide for good adhesive coating.

Referring now to the preferred embodiment illustrated in FIG. 3, certain desirable relationships between the structural elements of the film will be appreciated. Specifically, the width of individual monofilaments is preferably from about 0.2 to 2.0 mm, and most preferably from about 0.5 to 1.5 mm. The distance between adjacent monofilaments, i.e., the length of the interconnecting fibrils, is preferably from one to four times and most preferably from one to two times the width of individual monofilaments. If the ratio of monofilament spacing to width is less than 1/1, average tape porosity approaches undesirably low values, while at ratios greater than about 4/1, the tape begins to lose dimensional stability. Also in a preferred embodiment, the monofilaments are spaced at about 3 to 6 per cm and the fibrils interconnecting the monofilaments are spaced at about 10 to 60, and preferably at 30 to 60 fibrils per cm.

The fibrillated film material preferably has a break elongation of from about 5 to 50 percent, and most preferably from about 10 to 40 percent. In surgical tape application, some elongation is desirable so the tape may conform to the body, but elongation values higher than about 50 percent which allow the tape to lose its shape and restraining power are not preferred. Likewise, in surgical applications, extremely high tensile strengths are not required for wound closure and may interfere with tearability of the tape. Tensile strengths of from about 2 to 4 kg per cm of tape width and tear strengths of less than 200 grams are generally considered to be satisfactory for most applications.

Polymer compositions useful as backing materials for the surgical tapes of the present invention are those thermoplastic fiber forming polymers and copolymers capable of being fabricated into expanded fibrillated films as herein described. Preferred polymers include the lower polyolefinic polymers such as polyethylene and polypropylene and copolymers of ethylene and propylene, with high density polyethylene and polypropylene being particularly preferred. Other suitable polymers include nylon 6 and nylon 66, polyesters such as poly(ethylene terephthalate), and acrylics such as polyacrylonitrile and copolymers of acrylonitrile and vinyl acetate. The polymeric film preferably has a thickness of from about 0.05 to 0.50 mm for application in the present invention, and most preferably from 0.1 to 0.3 mm.

The adhesive for use with the novel backing material of the present invention may be any non-toxic, pressure sensitive adhesive which is preferably permeable to gas and water vapor. Pressure sensitive adhesives, i.e., adhesives which are inherently tacky, viscoelastic and cohesive in the normal dry state, and which are also non-toxic, non-irritating, and suitable for use in surgical, dermatological or cosmetic applications are well-known in the art. Some examples of representative materials suitable for use as adhesive coatings for surgical tapes as given in U.S. Pat. No. 3,645,835, incorporated herein by reference, include blends of vinyl ether or acrylic polymers, hydroxy acrylate polymers, polyvinyl ethyl ethers, and acrylates ester copolymers containing hydrophillic groups. Other suitable adhesives include rubber based adhesives such as polyisobutylene and mixtures of polyisobutylene with natural rubber, and the rubbery copolymer of isoctyl acrylate and acrylic acid in a 94 : 6 ratio as described in U.S. Pat. Nos. 2,884,126 and 3,121,021, both of which patents are incorporated herein by reference.

The adhesive is preferably applied to the fibrillated film backing material at a level of from about 40 to 100 g/m$^2$. Application is conveniently accomplished by a transfer process wherein the adhesive solution is spread on release coated paper, dried and partially cured, and then contacted with the backing material under sufficient pressure to ensure good bonding. The release paper is then removed and the adhesive further dried or cured if necessary. The application of adhesive to surgical tapes by transfer coating is described in U.S. Pat. Nos. 3,121,021 and 3,645,835 incorporated above by reference.

The adhesive coating may be porous conforming to the porous pattern of the backing material, or the adhesive may bridge the pores of the backing material to appear as a substantially continuous coating, or the coating may be partially porous and partially continuous. Where the adhesive layer conforms to the porous pattern of the backing material, the final tape product will have high vapor and liquid transmission rates desirable for certain surgical applications. Where the adhesive layer is visibly continuous over the surface of the tape, the adhesive is preferably microporous to facilitate transmission of moisture vapor as described in U.S. Pat. No. 3,121,021. Other adhesives which are highly polar and thus allow rapid diffusion of gas and moisture vapor through the adhesive layer may be substantially non-porous. The adhesive is not to be limited by composition or by pore size, or by the porosity of the adhesive layer so long as the adhesive coated tape is sufficiently permeable to moisture vapor, air and gases generated at the wound site to prevent occlusion of moisture under the tape which leads to maceration and irritation of the skin.

The porosity of the adhesive layer can be increased by applying the adhesive under conditions favorable to the formation of bubbles in the adhesive layer. When the adhesive is applied to the release paper from a solvent solution, failure to dry the coated paper sufficiently to completely remove the solvent results in the formation of bubbles in the adhesive layer. When the adhesive is transferred to the tape backing material, the bubbles are partially collapsed, particularly in the area of the solid monofilament ribs of tape. The bubbles in the porous fibril area of the tape rupture as the tape is handled and applied to the wound site and dramatically increase the net porosity of the tape.

The present invention is further described by the following examples which are presented for purposes of illustration only and are not limiting of the invention.

EXAMPLE I

A 0.11 mm film of polypropylene was embossed with a series of substantially uniformly spaced parallel striations running longitudinally thereof, and mechanically fibrillated and expanded in a direction transverse to the longitudinal axis of the striations to yield a porous film comprised of continuous monofilaments 0.48 mm wide, spaced 0.84 mm apart, and interconnected by approximately 55 fibrils per cm. The openings defined by the fibrils were about 0.1 x 0.84 mm and the total open area of the film was about 55 percent. The film had a tensile strength of 3.1 kg/cm of width and a break elongation of 40 percent in a direction normal to the orientation of the monofilaments. The film was bilaterally tearable with tear strengths as determined by the Elmendorf Tear Test according to ASTM Method D-689 of 48 g in a direction normal to the monofilaments, and 88 g in a direction parallel to the monofilaments.

The fibrillated film was coated on one side with about 50 g/m² of a visually continous film of a pressure sensitive cross-linkable adhesive comprising an ethyl acrylate polymer. The adhesive layer was applied by transfer coating from release paper using conventional techniques. Specifically, the adhesive was coated onto the release paper from a solvent solution at a thickness controlled to provide 47 g/m² dry adhesive. The coated paper was oven dried and cured at about 170° C for about 1.5 minutes. The cured adhesive was transferred to the plastic backing material by hot laminating at about 80° C.

The coated film was slit in a direction perpendicular to the monofilaments to provide strips 1 cm wide, and the strips were cut to 10 cm lengths for use as surgical tape. When applied to skin, the tape gave satisfactory results and did not produce skin maceration due to occlusion of moisture.

EXAMPLE II

The tape of Example I was immersed in a normal saline solution for 30 minutes at 27° C. The change in tensile properties were compared to those obtained with a conventional tape of the prior art constructed with a rayon thread reinforced non-woven cellulosic backing material.

|  | Tensile, kg/cm | | Elongation, Percent | |
| --- | --- | --- | --- | --- |
|  | Dry | Wet | Dry | Wet |
| Tape of Example I | 3.1 | 3.2 | 40 | 40 |
| Control | 3.4 | 1.6 | 21 | 35 |

It is apparent from the above data that the surgical tapes of the present invention are substantially unaffected by extended exposure to moisture.

EXAMPLE III

The tape of Example I was evaluated for rate of water vapor transmission (WVT) at 100° F (37.8° C) and 90 percent relative humidity according to ASTM Method E96-66 (Procedure E), and for air porosity as measured on a Gurley Air Porosity Meter by determining the time required for 100 cc of air at 4.9 inches water pressure to pass through 1 sq. inch of porous sheet material. Conventional non-woven cellulosic surgical tape and conventional woven surgical tape were also tested as comparative controls with the following results:

|  | W.V.T. g/m²/24 hrs. | Air Porosity Seconds |
| --- | --- | --- |
| Tape of Example I | 1057 | 3.8 |
| Non-woven control | 3413 | 3.0 |
| Woven control | 861 | 186 |

Water vapor transmission rates in excess of 500 are generally recognized to be satisfactory for surgical tapes, wound coverings and dressings, as discussed for example in U.S. Pat. No. 3,645,835. In the case of the present invention, the barrier to both water vapor transmission and air porosity is due exclusively to the adhesive coating and may be varied by regulating the compositon and/or thickness of the adhesive.

EXAMPLE IV

Two films of polypropylene identified as Film A and Film B were embossed with a series of substantially uniformly spaced parallel striations running longitudinally thereof, and mechanically fibrillated and expanded in a direction transverse to the longitudinal axis of the striations to yield a porous film comprising a series of continuous monofilaments interconnected by a plurality of parallel fibrils oriented at right angles to the monofilaments. The physical structure and properties of the films are compared to those of the film of Example I as follows:

| Film | Film Thickness | Monofilaments | | Fibrils | | | Physical Properties | | |
| --- | --- | --- | --- | --- | --- | --- | --- | --- | --- |
|  |  | Width | Spacing | Width | Frequency | Spacing | Tensile* | Elongation* | Porosity |
| A | 0.28 mm | 1.20 mm | 1.81 mm | 0.70 mm | 8/cm | 0.55mm | 3.32 kg/cm | 11% | .32% |
| B | 0.19 | 1.27 | 1.54 | 0.13 | 40 | 0.12 | 2.36 | 16 | 23 |
| Ex I | 0.11 | 0.48 | 0.84 | 0.08 | 55 | 0.10 | 3.07 | 40 | 55 |

*measured in a direction normal to orientation of monofilaments.

Films A and B, when coated with an adhesive as described in Example I, produce a porous surgical tape which is dimensionally stable, bilaterally tearable, unaffected by moisture and body fluids, and otherwise conforming to the described properties of tapes of the present invention.

The present invention contemplates the use of highly fibrillated porous polymeric film as a backing material for surgical tape. Many variations in structural design of the backing material, in the method of manufacture, and in adhesive compositions and method of application will be apparent to those skilled in the art, and such variations are included within the scope of the present invention.

What is claimed is:

1. A moisture vapor permeable, pressure sensitive adhesive tape comprising a porous film backing material coated on one surface with a pressure sensitive adhesive, said backing material comprising a patterned and fibrillated thermoplastic, fiber forming polymeric film having a plurality of substantially parallel continuous monofilaments interconnected by a plurality of fibrils extending between adjacent monofilaments, said fibrils and said monofilaments defining rows of openings between adjacent monofilaments, the total open area of said film being from about 10 to 70 percent.

2. A tape of claim 1 wherein the distance between adjacent monofilaments is from one to four times the width of individual monofilaments.

3. A tape of claim 1 wherein adjacent monofilaments are interconnected by about 10 to 60 fibrils per cm.

4. A tape of claim 1 wherein the individual monofilaments have a width of from about 0.2 to 2 mm.

5. A tape of claim 1 wherein the monofilaments have a thickness of from 0.05 to 0.5 mm.

6. A tape of claim 1 wherein the fibrils extend at substantially right angles between adjacent monofilaments.

7. A tape of claim 1 wherein the monofilaments extend across the width of the tape.

8. A tape of claim 1 wherein the monofilaments extend along the length of the tape.

9. A tape of claim 1 wherein the polymeric film is a lower polyolefinic polymer.

10. A tape of claim 9 wherein the polyolefinic polymer is selected from the group consisting of polypropylene and polyethylene.

11. A tape of claim 9 wherein the polyolefinic polymer is a copolymer of propylene and ethylene.

12. A tape of claim 1 wherein the adhesive layer is visually continuous and porous to water vapor.

13. A tape of claim 1 wherein the adhesive layer has openings corresponding to the openings between adjacent monofilaments in the polymeric film.

14. A moisture vapor permeable, pressure sensitive surgical adhesive tape comprising a porous film backing material coated on one surface with a pressure sensitive adhesive, said backing material comprising a patterned and fibrillated thermoplastic, fiber forming polymeric film having a plurality of substantially parallel continuous monofilaments interconnected by a plurality of fibrils extending at substantially right angles between adjacent monofilaments, said fibrils and said monofilaments defining rows of openings between adjacent monofilaments, the total open area of said film being from about 25 to 55 percent.

15. A tape of claim 14 wherein the individual monofilaments have a width of from about 0.5 to 1.5 mm and the distance between adjacent monofilaments is from one to two times the width of the individual monofilaments.

16. A tape of claim 14 wherein adjacent monofilaments are interconnected by about 30 to 60 fibrils per cm.

17. A tape of claim 14 wherein the monofilaments have a thickness of from 0.05 to 0.5 mm.

18. A tape of claim 14 wherein the monofilaments extend across the width of the tape.

19. A tape of claim 18 having a tensile strength of at least 2 kilograms per centimater of tape width and an elongation of between about 10 and 40 percent in the direction of the length of the tape.

20. A tape of claim 14 wherein the monofilaments extend along the length of the tape.

21. A tape of claim 14 wherein the polyolefinic film is polypropylene.

22. A tape of claim 14 wherein the adhesive layer is visually continuous and porous to water vapor.

23. A tape of claim 14 wherein the adhesive layer has openings corresponding to the openings between adjacent monofilaments in the polymeric film.

* * * * *